United States Patent [19]

Kaji et al.

[11] Patent Number: 5,302,725
[45] Date of Patent: Apr. 12, 1994

[54] ARYL TRIFLATE COMPOUNDS AND RADIOLOGICALLY ACID PRODUCING AGENTS THEREOF

[75] Inventors: Makoto Kaji, Hitachi, Japan; S. Peter Pappas, West Hartford, Conn.

[73] Assignee: Hitachi Chemical Co., Ltd., Tokyo, Japan

[21] Appl. No.: 963,754

[22] Filed: Oct. 20, 1992

Related U.S. Application Data

[62] Division of Ser. No. 790,169, Oct. 18, 1991, Pat. No. 5,198,402.

[51] Int. Cl.$^5$ .......................................... C07D 209/48
[52] U.S. Cl. .................................... 548/479; 548/476; 558/46; 558/47; 558/54
[58] Field of Search ................ 558/46, 47, 54; 548/476, 479

[56] References Cited

U.S. PATENT DOCUMENTS 3,346,612  10/1967  Hansen .................................. 558/54

FOREIGN PATENT DOCUMENTS 0442495  8/1990  European Pat. Off. .

OTHER PUBLICATIONS

Synthesis; No. 2; Feb. 1982; Stuttgart DE; pp. 85–126; P. J. Stang. et al.
Chemical Abstracts; vol. 115, No. 21; Nov. 25, 1991; p. 908 Abstract 115:231872v.
Tetrahedron Letters; vol. 31; No. 24; 1990; Oxford GB; pp. 3421–3424.
Journal of the Chemical Society; Perkin Transactions 1; No. 7; Jul. 1989; Letchworth GB; pp. 1365–1366.
Chemical Abstracts; vol. 111; No. 25; Dec. 18, 1989; p. 760 Abstract 111:232502d.
Chemical Abstracts; vol. 108; No. 17; Apr. 25, 1988; p. 722 Abstract 108:150229u.
Chemical Abstracts; vol. 111; No. 13; Sep. 25, 1989; p. 662 Abstract 111:115161f.
Chemical Abstracts; vol. 109; No. 26; Dec. 26, 1988; p. 725 Abstract 109:241505t.
Journal of the American Chemical Society; vol. 109; No. 9; Apr. 29, 1987; Gaston, Pa.; pp. 2831–2833.
Chemistry Letters; No. 3; 1991; Tokyo JP; pp. 459–460.
European Journal of Medicinal Chemistry Chimica Therapeutica; vol. 18; No. 2; 1983; Paris, FR. pp. 107–111.
Tetrahedron Letters; vol. 28; No. 13; 1987; Oxford GB; pp. 1381–1384.
Chemical Abstracts; vol. 116, No. 14; Apr. 6, 1992; p. 9 Abstract 116:129789g.
Journal of Organic Chemistry; vol. 57; No. 5; Feb. 28, 1992; Easton US; pp. 1481–1486.
Chemical Abstracts; vol. 113; No. 16; Oct. 15, 1990; p. 699 Abstract 113:142315g.
Macromolecules; vol. 23; No. 1; Jan. 8, 1990; Easton US; pp. 145–150.

Primary Examiner—Mary C. Lee
Assistant Examiner—Jacqueline Haley
Attorney, Agent, or Firm—Antonelli, Terry, Stout & Kraus

[57] ABSTRACT

Aryl triflate compounds can generate a strong acid when exposed to irradiation of radiation and can be used as an acid generator in a radiologically-acid-producing agent system and a radiosensitive composition.

3 Claims, 2 Drawing Sheets

ARYL TRIFLATE COMPOUNDS AND RADIOLOGICALLY ACID PRODUCING AGENTS THEREOF

This application is a divisional application of application Ser. No. 790,169, filed Oct. 18, 1991 now U.S. Pat. No. 5,198,402.

BACKGROUND OF THE INVENTION

The present invention relates to a radiosensitive composition which can be utilized in coating materials, printing materials, UV ink, photoresists for semiconductors, photoresists for printed circuit board, materials for holography, etc.; and an aryl triflate compound, an photo-acid-producing (or generating) agent (or photo acid generator) or an photo-acid-producing agent system, which is suitable for said radiosensitive composition.

Practical use of photochemical cationic polymerization was made possible by use of a thermally stable onium salt found by J. V. Crivello (J. V. Crivello and J. H. Lam, Macromolecules, vol. 10, p. 1307 (1977), etc.). In the photochemical cationic polymerization, as compared with conventionally used photochemical radical polymerization, the polymerization is not inhibited by air and the lifetime of an active species is longer. Therefore, the photochemical cationic polymerization is advantageous, for example, in that living polymerization is possible and monomers can be selected in a wide range. Accordingly, earnest studies are in progress in this field. Recent results of investigation on the photochemical cationic polymerization are reviewed in detail in UV Curing: Science and Technology, vol. 1 (1978) and vol. 2 (1984), Technology Marketing Corporation, Norwalk, Conn. A so-called chemical amplified photoresist has been proposed by a group belonging to International Business Machines Corp. The chemical amplified photoresist is highly pervious to excimer laser and has high sensitivity and resolution. Therefore, it is noted as a photoresist for microfabrication of a semiconductor (M. J. Bowden and S. R. Turner, "Polymers for High Technology Electronics and Photonics," ACS Symposium Series, U.S. Chemical Society, Washington, D.C. (1987) p. 138, etc.).

Both photochemical cationic polymerization system and chemical amplification system comprise as their essential constituent a compound or a system, which produces a strong acid on light irradiation. In the case of heretofore known onium salts such as triaryl sulfonium salts and diaryl iodonium salts, the quantum yield of acid production is relatively high and the strength of an acid produced is sufficient, but the onium salts are disadvantageous, for example, in that a light source is limited because wavelengths at which they are photosensitive are short, that they have a bad compatibility with generally used resin systems, that they contain metals, resulting in doping unnecessary in the semiconductor field, and that soft errors due to radioisopes take place. Efforts have been made in various fields to overcome these disadvantages. For example, S. P. Pappas, i.e., one of the present investors, and his co-workers found that the onium salts are photochemically sensitized by anthracene and the like, whereby application of the onium salts in the near ultarviolet range was made possible (S. P. Pappas, Journal of Polymer Science, Polymer Chemistry Edition, vol. 22, P. 77-84 (1984). There was attempted a method in which the onium salts were improved in compatibility with resin systems by introducing an alkyl group into the aryl group. In the process disclosed in Japanese Patent Unexamined Publication No. 63-272977, application of the onium salts in the semiconductor field is made possible by converting them into onium salts which contain a counter ion but not a metal.

Acid-producing agents other than the onium salts have also been investigated. For example, there have been disclosed cases in which there are used o-nitrobenzyl tosylate (L. F. Thompson, E. Reichmanis, F. M. Houlikan and R. G. Tarascon, Proceedings of the ACS Division Polymeric Materials: Science and Engineering, vol. 60, p. 137 (1989)), trichloromethyl-s-triazine (Japanese Patent Unexamined Publication Nos. 61-169835 and 61-169837), and a sulfonyl compound (Japanese Patent Unexamined Publication No. 61-166544). However, when these acid-producing agents are used, the strength of acids produced is not sufficient. There are also known mix ligand arene cyclopentadienyl Fe (II) salts (J. Lohse and H. Zweifel, Advances in Polymer Science, vol. 78, p. 61 (1986)), but they are not free from the defects described above, namely, they contain a metal and are ionic. Thus, there is not known a radiologically-acid-producing agent which can be subjected to spectral sensitization for impartment of sensitivity to a generally used radiation source, contains neither ionic bond nor metal atom, has a sufficiently high efficiency of acid production by radiation irradiation, gives an acid having a high strength, and has a high storage stability.

SUMMARY OF THE INVENTION

The present invention relates to a radiologically-acid-producing agent or a radiologically-acid-producing system, which have these required characteristics, an aryl triflate compound capable of giving said agent or system, and a photosensitive composition using said agent or system.

The present invention provides an aryl triflate compound of the general formula (I) or (II):

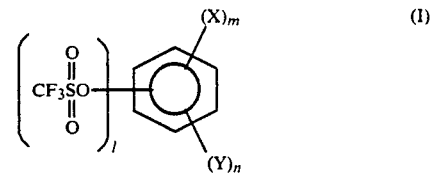
(I)

wherein X is an alkoxycarbonyl group, a cyano group, a nitro group or a trifluoromethyl group; Y is a hydrogen atom, a halogen atom, a linear or branched alkyl group, an aralkyl group, or a substituted or unsubstituted phenyl group; e is an integer of 1 to 5; m is an integer of 1 to 5; and n is zero or an integer of 1 to 4, l, m and n being chosen so that l+m+n=6,

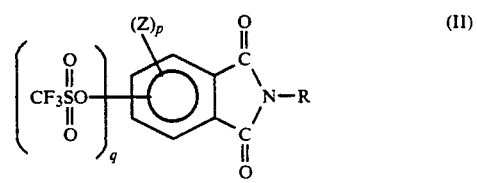
(II)

wherein R is a linear or branched alkyl group having 1 to 22 carbon atoms, an aralkyl group having 7 to 22 carbon atoms, or a substituted or unsubstituted phenyl group; Z is a hydrogen atom, a halogen atom or an alkyl group; q is an integer of 1 to 4; and p is zero or an integer of 1 to 3, p and q being chosen so that p+q=4.

The present invention also provides an aryl triflate compound of the general formula:

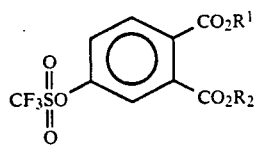
(III)

wherein $R^1$ and $R^2$ are independently a linear or branched alkyl group having 1 to 22 carbon atoms, an aralkyl group having 7 to 22 carbon atoms, or a substituted or unsubstituted phenyl group.

The present invention further provides an aryl triflate compound of the general formula:

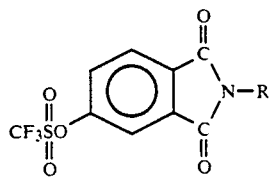
(IV)

wherein R is a linear or branched alkyl group having 1 to 22 carbon atoms, an aralkyl group having 7 to 22 carbon atoms, or a substituted or unsubstituted phenyl group.

The present invention still further provides a radiologically-acid-producing agent comprising any one of the aryl triflate compounds of the formulae (I) to (IV).

The present invention still provides a radiologically-acid-producing agent system comprising any one of the aryl triflate compounds of the formulae (I) to (IV), and at least one sensitizer.

The present invention also provides a radiosensitive composition comprising any one of the aryl triflate compounds of the formulae (I) to (IV), and a compound which reacts in the presence of an acid.

DESCRIPTION OF THE PREFERRED EMBODIMENTS

Figure 1:
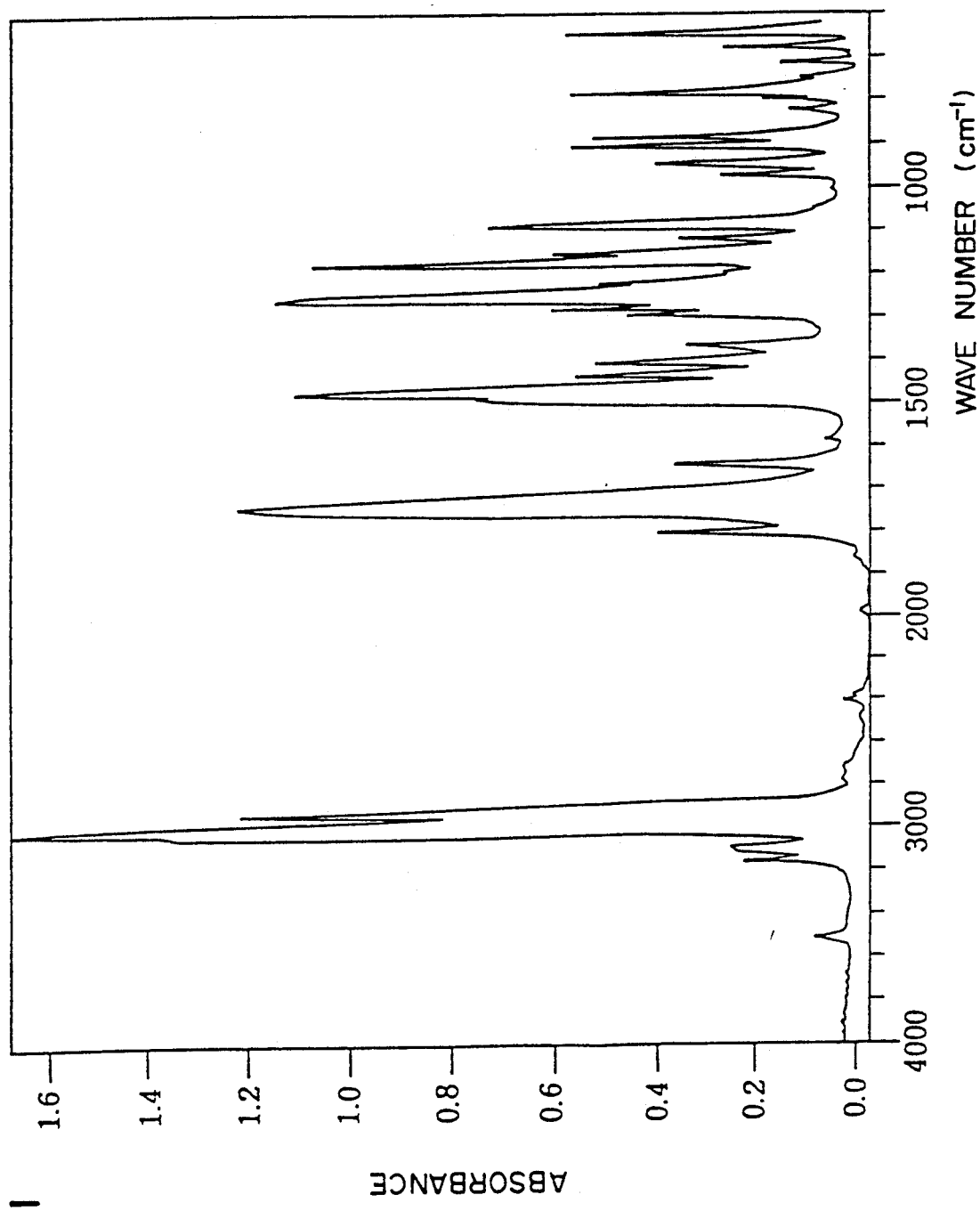
FIGS. 1 and 2 are infrared absorption spectra of DMPhTf and NBITF, respectively.

The aryl triflate compound of the present invention is represented by the general formula (I) or (II):

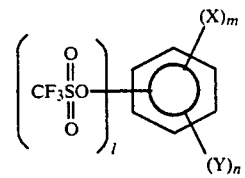
(I)

wherein X is an alkoxycarbonyl group, a cyano group, a nitro group or a trifluoromethyl group; Y is a hydrogen atom, a halogen atom, a linear or branched alkyl group preferably having 1 to 22 carbon atoms, an aralkyl group preferably having 7 to 22 carbon atoms, or a substituted or unsubstituted phenyl group wherein the number of substituent is preferably 1 to 5 and the substituents are independently preferably a halogen atom, a cyano group, a straight or branched alkyl group preferably having 1 to 22 carbon atoms, or an alkoxy group preferably having 1 to 20 carbon atoms; l is an integer of 1 to 5; m is an integer of 1 to 5; and n is zero or an integer of 1 to 4, l, m and n being chosen so that l+m+n=6,

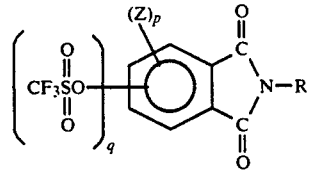
(II)

wherein R is a linear or branched alkyl group having 1 to 22 carbon atoms, an aralkyl group having 7 to 22 carbon atoms, or a substituted or unsubstituted phenyl group, the substituent being the same as defined in Y; Z is a hydrogen atom, a halogen atom or an alkyl group preferably having 1 to 22 carbon atoms; q is an integer of 1 to 4; and p is zero or an integer of 1 to 3, p and q being chosen so that p+q=4.

The present invention further relates to a radiologically-acid-producing agent comprising said compound, and a radiologically-acid-producing agent system and a radiosensitive composition which use said compound.

The aryl triflate compound is preferably an aryl triflate compound of the general formula (III):

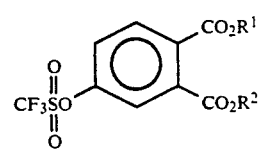
(III)

wherein $R^1$ and $R^2$ are independently a linear or branched alkyl group having 1 to 22 carbon atoms, an aralkyl group having 7 to 22 carbon atoms, or a substituted or unsubstituted phenyl group, or an aryl triflate compound of the general formula (IV):

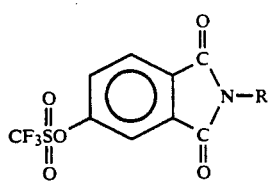
(IV')

wherein R is a linear or branched alkyl group having 1 to 22 carbon atoms, an aralkyl group having 7 to 22 carbon atoms, or a substituted or unsubstituted phenyl group.

The novel aryl triflate compound of the present invention contains neither ionic bond nor metal ion and hense can be used for various purposes. Trifluoromethanesulfonic acid which said compound produces on radiation irradiation is a superstrong acid, that is, said compound provides a sufficiently strong acid.

The aryl triflate of the present invention can be obtained, for example, by condensing 1 equivalent weight of a corresponding phenol:

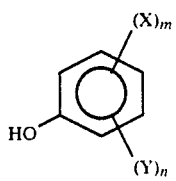

wherein X and Y are as defined above; m is an integer of 1 to 5; and n is zero or an integer of 1 to 4, m and an being chosen so that m+n=5, or

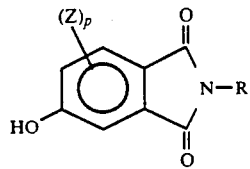

wherein R and Z are as defined above; and p is zero or an integer of 1 to 3, with 1.1 equivalent weight of trifluoromethanesulfonic anhydride $(CF_3SO_2)_2O$ in anhydrous pyridine (L. R. Subramanian, M. Hanack, L. W. K. Chang, M. A. Imhoff, P. V. R. Schleye, F. Effenberger, W. Kurtz, P. J. Stang and T. E. Dueber, Journal of Organic Chemistry, vol. 40, p. 4099, (1976)).

Examples of the compound of the formula (I) or (II) are p-nitrophenyl triflate, m-nitrophenyl triflate, o-nitrophenyl triflate, 2,4-dinitrophenyl triflate, p-cyanophenyl triflate, m-cyanophenyl triflate, o-cyanophenyl triflate, 3,4-dicyanophenyl triflate, 3,4-bis(methoxycarbonyl)phenyl triflate, 3,4-bis(ethoxycarbonyl)phenyl triflate, 3,4-bis(n-propoxycarbonyl)phenyl triflate, 3,4-bis(n-butoxycarbonyl)phenyl triflate, 3,4-bis(octoxycarbonyl)phenyl triflate, p-trifluoromethylphenyl triflate, m-trifluoromethylphenyl triflate, o-trifluoromethyl triflate, 4-(N-n-butylphthalimido)-yl triflate, 4-(N-phenylphthalimide)-yl-triflate, 4-(N-ethylphthalimido)-yl-triflate, 4-[N-(4'-cyanophenyl)phthalimido]-yl-triflate, 4-[N-(4'-methylphenyl)phthalimido]-yl-triflate, and 4-[N-(4'-bromophenyl)phthalimido]-yl-triflate. These aryl triflate compounds are useful as radiologically-acid-producing agents which are decomposed by irradiation with radiation such as X-rays, ultraviolet rays, electron beams or the like to produce an acid.

A radiologically-acid-producing agent system obtained by combining any of these triflates with a suitable sensitizer is sensitive at suitable wavelengths of a radiation source, so that it can have a high sensitivity. Therefore, the combination is desirable. As the sensitizer, known ones can be used in the present invention. Among them, electron-donative sensitizers are preferable. The electron-donative sensitizers includes, for example, Michaler's ketone, 4,4''-bis(diethylamino)benzophenone, pyrene, anthracene, 9-methylanthracene, 9-methoxyanthracene, 9,10-dimethylanthracene, 9,10-dimethoxyanthracene, 9-bromoanthracene, 1-methoxyanthracene, 2-methoxyanthracene, 1,4-dimethoxyanthracene, perylene, naphthalene, α-methoxynaphthalene, and β-methoxynaphthalene. It is particularly preferable to use at least one sensitizer selected from anthracene, 9-methoxyanthracene and 9,10-dimethoxyanthracend. The ratio of the aryl triflate compound to the sensitizer is usually 1/9 to 10/0 by weight.

The aryl triflate of the present invention or the radiologically-acid-producing agent or agent system obtained by combining the aryl triflate with at least one sensitizer is made into a radiosensitive composition which produces a reaction product on radiation irradiation, by combining the aryl triflate or the agent or agent system with a compound which reacts in the presence of an acid.

The radiosensitive composition is useful in the above-mentioned coating materials, printing matrices and the like.

As the compound which reacts in the presence of an acid, there are used, for example, compounds having a group which permits cationic polymerization in the presence of an acid, compounds having a group which permits crosslinking in the presence of an acid, and compounds having a bond which is cleaved in the presence of an acid.

As described in Toshinobu Higashimura, "Cationic Polymerization", Koza Jugo Hannoron, vol. 3, after p. 3, Kagaku Dojin (1971), the compounds having a group which permits cationic polymerization in the presence of an acid include styrene, vinyltoluene, N-vinylcarbazole, N-vinylpyrrolidone, various vinyl ethers, various vinylidene compounds, vinylene compounds (e.g. 2-methyl-2-butene), conjugated dienes (e.g. 1,3-butadiene), cyclic unsaturated compounds (e.g. indene and cyclopentadiene), acetylene compounds (e.g. phenylacetylene), aldehydes, isonitriles, oxirane compounds, tetrahydrafuran compounds, oxetane compounds, trioxane compounds, β-propiolactone compounds, aziridine compounds, etc. Various epoxy monomers or prepolymers which are industrially easily available are also preferably used. They include, for example, various epoxy resins derived from bisphenol A and epichlorohydrin (e.g. Epikote 828, a trade name, Shell Chemical Co.), 3,4-epoxycyclohexylmethyl-3',4'-epoxycyclohexanecarboxylate (Araldite CY179, a trade name, Ciba-Geigy Co.), diglycidyl hexahydrophthalate (Araldite CY184, a trade name, Ciba-Geigy Co.), diglycidyl 1,2,3,6-tetrahydrophthalate (Araldite CY192, a trade name, Ciba-Geigy Co.), N,N,N',N'-tetraglycidyl-m-xylenediamine (TETRAD-X, a trade name, mfd. by Mitsubishi Gas Chemical Co. Inc.), 1,3-bis(N,N-diglycidylaminomethyl)cyclohexyne (TETRAD-C, a trade name, Mitsubishi Gas Chemical Co. Inc.), and various epoxy resins derived from cresol (or phenol) novolac resins and epichlorohydrin (e.g. EOCN series, trade names, Nippon Kayaku Co., Ltd.). There are also preferably used homopolymers obtained by polymerizing an acrylic monomer having an epoxy group, such as glycidyl acrylate or glycidyl methacrylate, or copolymers obtained by using such a monomer as a comonomer.

The compounds having a group which permits crosslinking in the presence of an acid include, for example, melamine resins such as hexamethoxymethylolmelamine and the like.

The compounds having a bond which is cleaved in the presence of an acid include, for example, poly(α-acetoxystyrenes); polydialdehydes; polyesters, polyethers, polycarbonates and polyacetals which are obtained by using as diol component, 1,4-(2-cyclohexenylene)diol, 1,4-dimethyl-2-butine-1,4-diol, 1,4-cyclohexanedial, 1,4-dimethylbutane-1,4-diol, 1,1,4,4-tetramethylbutane-1,4-diol, p-xylylenediol, bisphenol A, etc.; and derivatives of poly(p-hydroxystyrene) which are obtained by use of t-butyl ether, t-butyl carbonate, tetarhydropyranyl ether, etc.

The radiosensitive composition of the present invention is changed in solubility in a developer by radiation irradiation and hence can be used as a positive type or negative type resist composition, depending on the kinds of the compound which reacts in the presence of an acid, and the developer. The proportion of the acid-producing-agent or the acid-producing agent system is usually 0.05 to 10% by weight based on the weight of the radiosensitive composition.

If necessary, the radiosensitive composition of the present invention may contain high-molecular-weight polymers such as acrylic resins, polystyrenes, polyesters, polyamides, polyolefin sulfones, cresol resins, phenolic resins, etc.

In addition, the radiosensitive composition of the present invention may contain additives such as leveling agents, which are known to the art.

In the radiosensitive composition, the using amounts of the aryl triflate compound and the compound which reacts in the presence of an acid are not critical and chosen depending on the change of polarity and molecular weight of the radiosensitive composition which is caused by radiation irradiation.

The action of the present invention is brought about as follows. The aryl triflate compound absorbs radiation and then undergoes transition to a high-energy state, and its Ar—OTf ($=-SO_2CF_3$) bond is cleaved to give triflate anion ($TfO^\ominus$), which becomes trifluoromethanesulfonic acid. When an electron-donative sensitizer is combined with the aryl triflate compound, aryl triflate radical anions produced by the transfer of electrons from the sensitizer which has absorbed radiation to fall into a high-energy state are decomposed to give triflate anions, whereby trifluoromethanesulfonic acid is produced.

The present invention is illustrated by way of the following Examples.

EXAMPLE 1 a) Synthesis of 4-hydroxy-N-n-butylphthalimide

In a 250-ml round bottom flask were placed 20.5 g (112.6 mmols) of 4-hydroxyphthalic acid, 8.2 g (112.6 mmols) of n-butylamine and 100 ml of absolute ethanol. After mixing, the resulting mixture generated heat gently. The mixture was sufficiently stirred until the solids were completely dissolved. The alcohol was distilled off under reduced pressure, after which the viscous liquid thus obtained was heated at 180° C. for about 3 hours with continuous extraction of water. After cooling, the residue was solidified. The solidified residue was dissolved in an ethyl acetate-benzene (1:1 by volume) mixed solvent, and the resulting solution was washed with water, an aqueous sodium carbonate solution and then water. The organic layer was dried over anhydrous magnesium sulfate, concentrated, and then cooled to obtain powder crystals having a slightly yellowish white color. The crystals were collected by suction filtration and dried. Yield: 18.5 g (75%), m.p. 126°–127° C. The product was determined to be 4-hydroxy-N-n-butylphthalimide by investigation of its structure by NMR and infrared absorption spectrum.

$^1H$ NMR ($CDCl_3$): $\delta(ppm)=0.80-1.83$ (m, 7H, butyl), 3.61 (t, 2H, —N—$CH_2$—, J=6.9 Hz), 7.09 (dd, 1H, 6-ArH, $J_{56}=8.1$ Hz, $J_{36}=2.5$ Hz), 7.25 (d, 1H, 3-ArH, $J_{36}=2.5$ Hz), 7.63 (d, 1H, 5 - ArH, $J_{56}=8.1$ Hz).

b) Synthesis of 4-(N-n-butylphthalimido)yl Triflate (NBITF)

In a 100-ml round bottom flask were placed 3.75 g (17 mmols) of 4-hydroxy-N-n-butylphthalimide and 30 ml of anhydrous pyridine (dried on CaH), and cooled with ice water, and 5.15 g (18 mmols) of trifluoromethanesulfonic anhydride was added dropwise over a period of about 2 hours with stirring by means of a magnetic stirrer. The stirring was continued at 0° C. for another 1 hour after completion of the dropwise addition. The reaction mixture was sealed in a container and allowed to stand overnight in a refrigerator (about 5° C.). It was then poured into ice water, and the solid thus precipitated was collected by filtration. The solid was dissolved in benzene, and the resulting solution was washed with water, a 3 wt % aqueous NAOH solution, and then water. The organic layer was dried, concentrated, and then cooled to obtain white powder. The powder was collected by suction filtration and dried to find that the yield was 4.08 g (12.1 mmols, 70.8%).

m.p. 68°–69° C., $^1H$ NMR ($CDCl_3$): $\delta(ppm)=0.78-1.85$ (m, 7H, butyl), 3.67 (t, 2H, N—$CH_2$—, J=6.6 Hz), 7.54 (dd. 1H, 6-ArH, $J_{36}=2.0$ Hz, $J_{56}=7.8$ Hz), 7.69 (d, 1H, 3-ArH, $J_{36}=2.0$ Hz), 7.89 (d, 1H, 5-ArH, $J_{56}=7.8$ Hz).

From these results, the compound obtained was confirmed to be NBITF.

EXAMPLE 2

Synthesis of 3,4-bis(methoxycarbonyl)phenyl Triflate (DMPhTf)

The title compound was synthesized in the same manner as for NBITF except for using dimethyl 4-hydroxyphthalate in place of 4-hydroxy-N-n-butylphthalimide. Thus, a colorless liquid was obtained.

$^1H$ NMR ($CDCl_3$): $\delta(ppm)=3.91$ (s, 3 H, ester), 3.92 (s, 3H, ester), 7.45 (dd, 1H, 6-ArH, $J_{25}=2.4$ Hz, $J_{56}=8.4$ Hz), 7.68 (d, 1H, 3-ArH, $J_{25}=2.4$ Hz), 7.82 (d, 1H, 5-ArH, $J_{56}=8.4$ Hz).

From these results, the compound obtained was confirmed to be DMPhTf.

EXAMPLE 3

Synthesis of 4-(N-phenylphthalimide)-yl-triflate (NPhITf)

4-Hydroxy-N-phenylphthalimide was synthesized from 4-hydroxyphthalic acid and aniline in the same manner as in Example 1, a). By the reaction of the synthesized compound with trifluoromethanesulfonic anhydride, 4-(N-phenylphthalimide)-yl-triflate (NPhITf) was synthesized.

m.p. 116.5°–117.5° C.

$^1H$ NMR ($CDCl_3$): $\delta(ppm)=7.28-7.53$ (m, 5H, N-phenyl), 7.68 (dd, 1H, 6-ArH, $J_{36}=2.0$ Hz, $J_{56}=8.1$ Hz), 7.84 (d, 1H, 3-ArH, $J_{36}=2.0$ Hz), 8.03 (d, 1H, 5-ArH, $J_{56}=8.1$ Hz).

Figure 2:
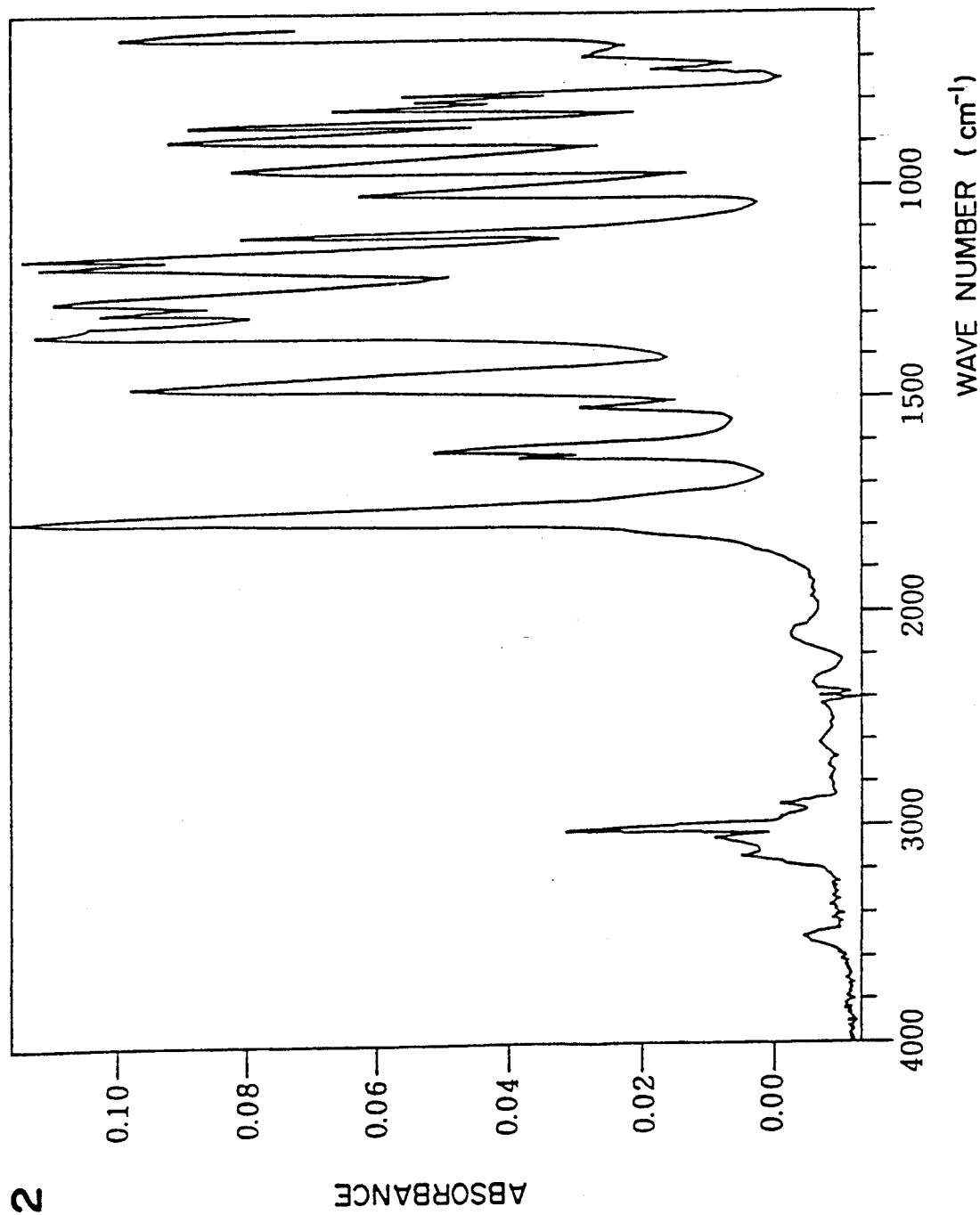

Infrared absorption spectra of NBITF and DMPhTf are shown in FIG. 1 and FIG. 2, respectively.

EXAMPLES 4 TO 7

Production of an acid by light irradiation was investigated by use of these aryl triflates. Solutions were prepared by using methylene chloride as solvent and each of the combinations shown in Table 1 of the aryl triflate (DMPhTf or NBITF) and a sensitizer selected from anthracene (An), 9-methoxyanthracene (9-MoA) and 9,10-dimethoxyanthracene (9,10-DMoA). Each solution was irradiated with monochromatic light having a wavelength of 365 nm and the acid thus produced was quantitatively determined. The monochromatic light having a wavelength of 365 nm was obtained by using a 450 W moderate pressure mercury arc lamp (Hanovia, Model 679-A36, mfd. by American Ace Co.) as light source and a 7-83 combination filter mfd. by Corning Glass Works. The light irradiation was carried out by use of a merry-go-round type photoreaction apparatus. The quantitative determination of the acid was carried out by the dye bleaching method by Gaines (G. E. L. Gaines, Analytical Chemistry, vol. 48, No. 2, p. 450 (1976)). The results obtained are shown in Table 1. The concentration of the aryl triflate was adjusted to $10^{-2}$M (mol/liter) and that of the sensitizer to each value shown in Table 1, whereby the absorbance was adjusted to 2.0 to 2.6.

TABLE 1

| Example | Optical acid production by aryl triflate | | | |
|---|---|---|---|---|
|  | 4 | 5 | 6 | 7 |
| Aryl triflate | DMPhTf | DMPhTf | DMPhTf | NBITf |
| Sensitizer | An | 9-MoA | 9,10-DMoA | 9-MoA |
| (sensitizer concentration, mol/liter) | ($9.46 \times 10^{-4}$) | ($3.18 \times 10^{-4}$) | ($3.69 \times 10^{-4}$) | ($3.18 \times 10^{-4}$) |
| Quantum yield of acid production | $2.16 \times 10^{-3}$ | $1.86 \times 10^{-3}$ | $3.03 \times 10^{-3}$ | $1.08 \times 10^{-3}$ |

The aryl triflate compound of the present invention produces a superstrong acid efficiently on radiation irradiation and hence is suitable as a material for a radiologically-acid-producing agent or a radiologically-acid-producing agent system. A radiosensitive composition comprising said aryl triflate compound can be used in photochemically cationic-polymerizable compositions and chemical amplification type resists and exhibit desirable characteristics.

What is claimed is:

1. An aryl triflate compound of the formula (II):

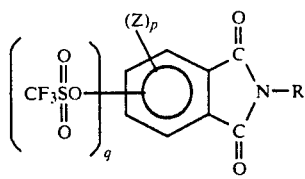

(II)

wherein R is a linear or branched alkyl group having 1 to 22 carbon atoms, an aralkyl group having 7 to 22 carbon atoms, or a substituted or unsubstituted phenyl group, the substituent being a halogen atom, a cyano group, a straight or branched chain alkyl group having 1 to 22 carbon atoms, or an alkoxy group having 1 to 20 carbon atoms; Z is a hydrogen atom, a halogen atom or an alkyl group; q is an integer of 1 to 4; and p is zero or an integer of 1 to 3, p and q being chosen so that p+q=4.

2. An aryl triflate compound of the formula:

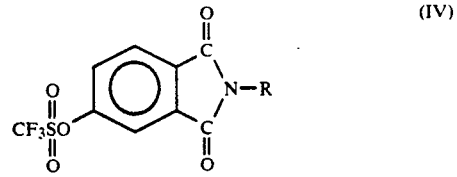

(IV)

wherein R is a linear or branched alkyl group having 1 to 22 carbon atoms, an aralkyl group having 7 to 22 carbon atoms, or a substituted or unsubstituted phenyl group, the substituent being a halogen atom, a cyano group, a straight or branched chain alkyl group having 1 to 22 carbon atoms, or an alkoxy group having 1 to 20 carbon atoms.

3. A radiologically-activated, acid-producing agent comprising an aryl triflate compound which produces an acid by exposure to radiation and which has the formula

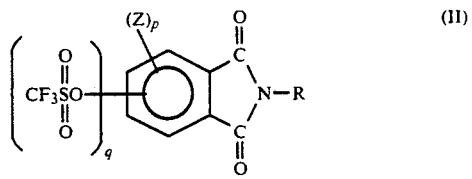

(II)

wherein R is a linear or branched alkyl group having 1 to 22 carbon atoms, an aralkyl group having 7 to 22 carbon atoms, or a substituted or unsubstituted phenyl group, the substituent being a halogen atom, a cyano group, a straight or branched chain alkyl group having 1 to 22 carbon atoms, or an alkoxy group having 1 to 20 carbon atoms; Z is a hydrogen atom, a halogen atom or an alkyl group; q is an integer of 1 to 4; and p is zero or an integer of 1 to 3, p and q being chosen so that p+q=4.

* * * * *